United States Patent [19]

Knapik et al.

[11] Patent Number: 4,582,803
[45] Date of Patent: Apr. 15, 1986

[54] STAGED IMMOBILIZED AMYLOGLUCOSIDASE AND IMMOBILIZED GLUCOSE ISOMERASE IN PRODUCING FRUCTOSE FROM THINNED STARCH

[75] Inventors: H. Peter G. Knapik, Bloomingdale; William H. Mueller, Darien, both of Ill.

[73] Assignee: UOP Inc., Des Plaines, Ill.

[21] Appl. No.: 619,741

[22] Filed: Jun. 11, 1984

[51] Int. Cl.$^4$ .............................................. C12P 19/24
[52] U.S. Cl. ....................................................... 435/94
[58] Field of Search ........................................... 435/94

[56] References Cited
U.S. PATENT DOCUMENTS
4,382,121  5/1983  Rohrbach et al. .................... 435/94

Primary Examiner—Lionel M. Shapiro
Attorney, Agent, or Firm—Thomas K. McBride; William H. Page, II; Eugene I. Snyder

[57] ABSTRACT

The limitation of an immobilized amyloglucosidase in hydrolyzing thinned starch to afford not more than about 93% glucose with isomaltose levels above about 1.5% can be overcome in a process for converting thinned starch to fructose using four closely coupled reactor stages. The first stage is a saccharification reactor using amyloglucosidase which converts thinned starch to a product containing from 50% to 85% glucose. This product is used in a first stage isomerization reactor, the effluent from which is sent to another saccharification reactor using immobilized amyloglucosidase where hydrolysis is continued until no more than about 6% disaccharides and higher oligosaccharides are present. Where this effluent is used as a feedstock for further conversion of glucose to fructose, it is operationally equivalent to a feedstock containing at least 94% glucose but with isomaltose levels under about 1.5%.

13 Claims, 2 Drawing Figures

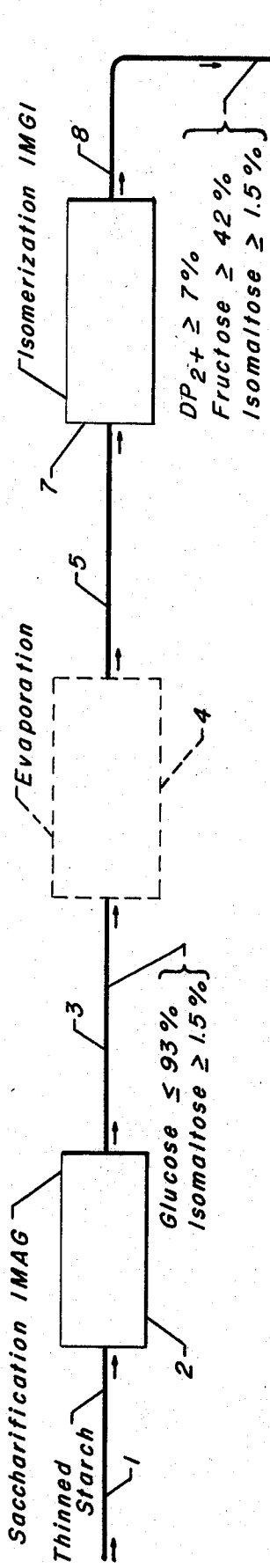
Figure 1 (Conventional Process Using IMAG)
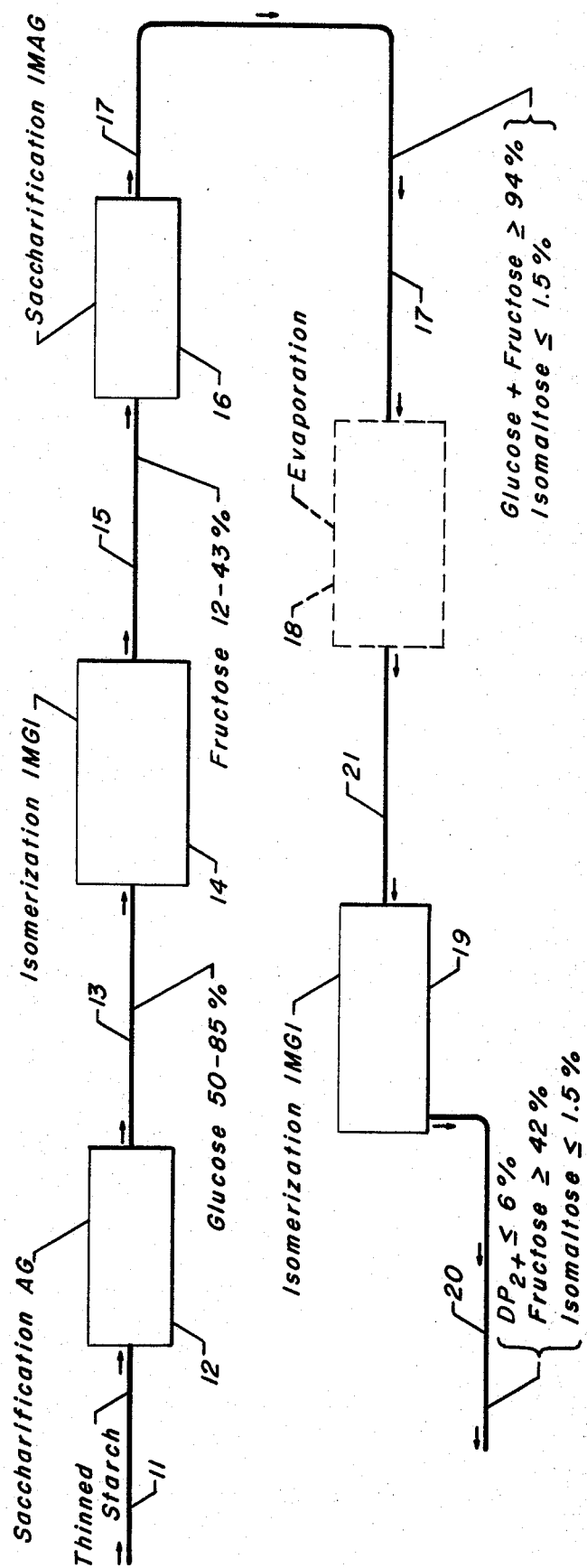
Figure 2 (Improved Process Using IMAG)

STAGED IMMOBILIZED AMYLOGLUCOSIDASE AND IMMOBILIZED GLUCOSE ISOMERASE IN PRODUCING FRUCTOSE FROM THINNED STARCH

BACKGROUND OF THE INVENTION

The commercial production of fructose utilizes three distinct processes. The first is the partial hydrolysis of starch, with corn starch being most commonly used, but cassava, tapioca, and rice also being sources, where most of the starch molecules are converted to lower molecular weight polysaccharides, to afford a product called thinned starch or starch hydrolysate. The second process is the hydrolysis of thinned starch to glucose (saccharification) and is generally an enzymatic hydrolysis mediated by amyloglucosidase. The third process is the isomerization of glucose to fructose catalyzed by the enzyme glucose isomerase to afford a product commonly containing 42-45% fructose. Generally the three processes are performed largely independent of each other, i.e., as three distinct and uncoupled processes carried out in the usual course of fructose production. Contrastingly, the subject matter of this application is a method of making fructose from thinned starch where the second and third processes described above are closely linked and cooperate to afford results unattainable from uncoupled systems.

In recent years the glucose-to-fructose conversion has been catalyzed by immobilized glucose isomerase. The use of immobilized enzymes is attended by diverse advantages, including reuse of the enzyme, thereby permitting its more efficient utilization, and elimination of an enzyme removal stage, as would be necessary for reuse of a soluble enzyme. However, the use of immobilized amyloglucosidase (IMAG) in enzymatic hydrolysis of thinned starch has not achieved commercial success because of several disadvantages for which previously there were no solutions. One disadvantage of IMAG processing is that the maximum glucose attainable is about 93% when a high activity IMAG is utilized, whereas commercial processes attain 94-6% glucose levels using soluble AG. Another disadvantage of IMAG is the formation of relatively high levels of reversion product, especially isomaltose, a bitter principal which seriously impairs the quality of the resulting glucose solution when subsequently used as a feedstock for fructose production. Reversion products are formed by the action of AG on glucose. Their formation is dependent on glucose concentration and reaction time; high glucose concentrations and long reaction times favor increased formation of reversion products.

We have been able to solve the dual problems of an unacceptably low maximum glucose concentration and an unacceptably high reversion product concentration attending the use of an immobilized amyloglucosidase using as a process flow scheme the partial hydrolysis of thinned starch by AG, either soluble or immobilized, to a product containing from about 50% to about 85% glucose, isomerizing the latter product with IMGI, hydrolyzing the isomerized product with IMAG to a product containing 6% or less of disaccharides and higher oligosaccharides ($DP_{2+}$), and isomerizing the saccharified stream with IMGI to the final desired fructose concentration. By conducting the initial hydrolysis to only partial conversion the accumulation of reversion products is reduced, both because the concentration of glucose is reduced and because a long reaction time is avoided. By conducting the second hydrolysis on a feedstock where glucose has been partially converted to fructose one avoids building up a high glucose concentration even where hydrolysis is conducted to the extent where not more than about 6% of disaccharides and higher oligosaccharides remain, and where the operational equivalent of at least 94% glucose has been attained, thereby tending to keep the accumulation of reversion product at reduced levels.

Thus the invention herein has the advantage of affording the operational equivalent of at least 94% glucose formation in the enzymatic hydrolysis of thinned starch using IMAG, a result heretofore unobtainable. A further advantage is that the equivalent of at least 94% glucose is formed by IMAG with a reduced level of isomaltose, a highly undesirable reversion product of glucose. Yet another advantage is that the scheme offers the potential of achieving superior results with an overall higher liquid hourly space velocity than a process using IMAG to maximum glucose formation followed by IMGI isomerization.

DESCRIPTION OF THE FIGURES

FIG. 1 depicts the flowscheme for an embodiment of a conventional process based on the prior art using IMAG for saccharification. FIG. 2 is the flowscheme of an embodiment of this invention.

DESCRIPTION OF THE INVENTION

The invention can be better understood by reference to FIG. 1, which is a flowscheme for use of IMAG in a conventional process, and its comparison with FIG. 2, which is a flowscheme for an improved process according to the invention herein. In the conventional process a feedstock of thinned starch, 1, enters a saccharification reactor, 2, containing IMAG. The feedstock is contacted with IMAG for a time sufficient to maximize glucose formation, with maximum glucose concentration generally not being more than about 93%. The effluent, 3, which contains up to about 93% glucose and more than about 1.5% of isomaltose, may be optionally sent to an evaporator, 4, where the dry solids content is increased prior to use of the material as a feedstock for fructose formation. Effluent from the evaporator, 5, or if no evaporation is performed effluent from the saccharification reactor, 3, may then be fed to the isomerization reactor, 7, for a time sufficient to give a product stream, 8, containing at least about 42% fructose for commercial purposes and which also contains more than about 1.5% isomaltose, and at least about 7% oligosaccharides ($DP_{2+}$).

In an embodiment of the improved process which is our invention a feedstock of thinned starch, 11, is sent to a saccharification reactor, 12, containing AG where hydrolysis is continued for a time sufficient to afford effluent, 13, containing from about 50% to about 85% glucose. The use of either soluble or immobilized AG in reactor, 12, is contemplated. After being adjusted to isomerization conditions, the effluent is used as the feedstock for the isomerization reactor, 14, containing IMGI where contact time is sufficient to isomerize from about 25% to about 50% of the glucose initially present to fructose. The effluent stream, 15, is then adjusted to saccharification conditions and used as a feedstock for a second saccharification reactor, 16, containing IMAG. Hydrolysis in the latter reactor is continued for a time sufficient to reduce the content of disaccharides and higher oligosaccharides to no more than about 6%, with the effluent stream, 17, containing at least 94% of the monosaccharides glucose and fructose and less than about 1.5% isomaltose. The effluent stream, 17, may then optionally be sent to an evaporator, 18, to increase its dry solids content prior to use as a feedstock for the final isomerization. The effluent, 17, or the concentrated material as the case may be, is adjusted to isomerization conditions and is used as the feedstock in isomerization reactor, 19, where contact with IMGI is for a time sufficient to give a product, 20, containing at least about 42% fructose but less than about 1.5% isomaltose.

The process which is our invention is one converting a feedstock of thinned starch to a product containing at least 94% monosaccharides as a mixture of glucose and fructose, less than about 1.5% isomaltose, and less than about 6% of total disaccharides and higher oligosaccharides. For convenience, all saccharides which are not monosaccharides will be designated as $DP_{2+}$. For the purpose of this application, thinned starch is a partially degraded starch containing a minor proportion of monosaccharides, up to about 10% but generally less than about 4%, and a distribution of polysaccharides, where from about 20% to about 70% are present as disaccharides ($DP_2$) through heptasaccharides ($DP_7$), with from about 30% to about 80% present as $DP_8$ and higher molecular weight polysaccharides. The percentages above are given on a dry solids basis. Thinned starch of commerce may contain from about 25% to about 45% dry solids, with the usual commercial product containing from about 25% to about 35% dry solids.

A feedstock of thinned starch is then hydrolyzed, or saccharified, using an amyloglucosidase. The particular source of the enzyme amyloglucosidase, whether it is used as the soluble or as the immobilized enzyme, and if immobilized the particulars of its method of immobilization, the specific support matrix used, and the resulting product which is immobilized amyloglucosidase is unimportant to the success of this invention. It is to be understood that wherever IMAG is designated it is used herein generically.

A feedstock of thinned starch is contacted with AG in the saccharification reactor under saccharification conditions. Saccharification conditions include a temperature from about 40° up to about 100° C. where the enzyme is sufficiently thermostable to permit such a process temperature, with a temperature of about 55°–60° C. being most usual within the range of 50°–70° C. At saccharifying conditions the pH generally is maintained between about 3.5 and 5.5, more usually between about 4.0 and 5.0.

An important aspect of our invention is that saccharification in the first reactor proceeds only to the extent of forming between about 50% to about 85% glucose, more usually between about 60% and about 80% glucose. This contrasts with prior art processes which conduct saccharification to maximum glucose formation, i.e., up to 95–96% for soluble AG and up to 90–93% for IMAG.

The product from the first saccharification reactor, which contains between about 50% and about 85% glucose, the remainder being $DP_{2+}$, is used as the feedstock for an IMGI reactor after adjustment to isomerizing conditions. The source of the enzyme glucose isomerase, the particular method of its immobilization, the support matrix used, and the particular product which is IMGI is not important to the success of this invention. Many variants are known to those skilled in the art, and although the various IMGI may not be equivalent, the use of any one of them is contemplated within the scope of this invention.

Isomerizing conditions include a temperature between about 40° and about 80° C., with a temperature near about 60° C. usually being practiced. Optimum pH generally is in the range between about 7.0 and 9.0. Various additives frequently are used in the feedstock, including, for example, magnesium ion, and sulfite or bisulfite.

The isomerization of glucose to fructose is an equilibrium reaction where there is about 50% conversion at equilibrium at about 60° C. The isomerization usually is not run to equilibrium, but instead at least about 25% of the glucose present is converted to fructose, and more typically isomerization is conducted for a time sufficient to convert from about 30% to about 45% of the glucose initially present to fructose. At one extreme, the effluent from the first isomerization reactor may contain as much as 50% $DP_{2+}$, the remainder being a mixture of glucose and fructose containing as little as about 12% fructose. At the other extreme, effluent from the reactor may contain as little as 15% $DP_{2+}$, the remainder being a mixture of glucose and fructose containing as much as about 43% fructose. In any case, this first isomerization step lowers glucose concentration by converting glucose to fructose and makes possible a more rapid and more complete conversion in the second saccharification reactor. The effluent from the first isomerization reactor is then adjusted to saccharifying conditions and used as a feedstock for a second saccharification reactor containing IMAG. Saccharification is performed as described above until there is no more than about 6% $DP_{2+}$ present. Of the latter material, not more than about one-fourth, or about 1.5% absolute, is isomaltose. The remainder of the saccharification effluent is a mixture of monosaccharides, glucose and fructose. It must be emphasized that this effluent when used as a feedstock for production of fructose is operationally equivalent to a feedstock from thinned starch where the hydrolysis has produced 94% or more glucose. It is in this second or final saccharification step wherein lie most of the advantages of this process scheme. By conducting the final stages of saccharification ($DP_{2+}$ hydrolysis) with lower glucose concentration two benefits are realized: first, the $DP_{2+}$ conversion proceeds more rapidly because product concentration (glucose) is lower; second, isomaltose formation is decreased because of the shorter reaction time and lower glucose concentration. The use of such a scheme allows production of a second stage saccharification product of 94–95% total $DP_1$ (glucose and fructose) at low isomaltose levels (<1.5%), whereas a conventional process using IMAG for saccharification affords a product containing only 90–93% glucose and over 1.5% isomaltose.

If the level of fructose in the effluent from the second saccharification reactor is sufficient, or if the effluent is to be used for some purpose other than isomerization of glucose to fructose, the effluent as a product can be recovered and processed for further use at this point. However, in the more usual case the effluent is used as a feedstock for a second stage isomerization reactor. When so used it is adjusted for isomerization conditions as described above. Contacting in the second isomerization reactor is generally for a time sufficient to afford an effluent product containing from about 30% to about 45% fructose, generally from about 42% to 45% fructose. The effluent is then recovered for further processing, if desired.

It is to be understood that the process which is our invention is susceptible of many variations which do not substantively alter the basic process, and which are, therefore, subsumed in the invention claimed. For example, there may be a concentration of an effluent or feedstock stream at one or more points. In commercial practice an IMGI uses a feedstock containing 45% dry solids, and one practicing the invention herein might prefer such conformity. As another example, where soluble AG is used it may be removed prior to the saccharification effluent entering the first stage of glucose isomerization. But it is to be emphasized that such variants, of which this is but one example, are within the scope of our invention.

EXAMPLE

Immobilized amyloglucosidase and glucose isomerase were prepared in accord with U.S. Pat. No. 4,141,857, the following detailed descriptions being exemplary and representative. Porous alumina of 60–80 mesh (45 g) was contacted with 101 ml of a 3.2 wt. % solution of polyethylenimine for 10 minutes, after which solid was collected and subsequently dried. The solid was contacted for 78 minutes with 1640 ml of a 4.7 wt. % solution of glutaraldehyde to cross-link the impregnated PEI. Liquid was decanted, and solid was washed with water to remove excess glutaraldehyde. The resulting support matrix was contacted with a sufficient amount of amyloglucosidase (CPC International G-990) to afford an IMAG with an activity of 680 IU/g at 90% product glucose (DSB) as measured by the assay below. The resulting IMAG was washed with a soluble starch solution to remove unbound enzyme, then divided into a 2.9 g reactor loading for the first IMAG column and a 9.8 g reactor loading for the second IMAG column.

Immobilized amyloglucosidase was assayed for AG activity by passing a 30 wt. % solution of Maltrin-150 over a 3 g bed of IMAG at 55° C. and pH 4.5. The flow rate was adjusted to produce 90 wt. % glucose (DSB). The number of micromoles glucose produced per minute per gram of IMAG is calculated and is the activity in IU/g IMAG.

Immobilized glucose isomerase was prepared by contacting a support matrix prepared as described above with a sufficient amount of glucose isomerase enzyme (CPC International G-993) to produce an IMGI having an activity of 1918 IU/g as measured by the assay described below. The resulting IMGI was washed a final time and divided into a 3.4 g reactor loading for the first IMGI column and 1.4 g loading for the second IMGI column.

A 0.05 g sample of IMGI in 16 ml of a solution containing 2.5 molar fructose, 5 mM magnesium ion and 0.5 mM Co(II) ion, buffered to pH 7.5 was incubated for 15 minutes at 60° C. with vigorous shaking. The glucose produced may be measured by any convenient means, such as a glucose analyzer. The activity in IU/g of IMGI is the number of micromoles of glucose produced per minute per gram IMGI.

The feedstock for the first saccharification reactor was Maltrin-150, which is a powdered, thinned starch supplied by Grain Processing Corporation, having a 15–17 dextrose equivalent. Analysis by high pressure liquid chromatography of a typical lot afforded the following saccharide distribution.

| Saccharide | Wt. % (dry solids basis, DSB) |
|---|---|
| $DP_1$ | 1.0 |
| $DP_2$ | 4.0 |
| $DP_3$ | 6.2 |
| $DP_4$ | 4.8 |
| $DP_5$ | 4.3 |
| $DP_6$ | 9.0 |
| $DP_7$ | 9.8 |
| $DP_8$ | 4.5 |
| $DP_{9+}$ | 56.3 |

The IMAG columns were operated at pH 4.5 and 55° C., and the IMGI reactors were operated at pH 8.0 at 60° C. The feedstock for the first IMAG reactor was Maltrin-150 containing 1000 ppm magnesium as magnesium sulfate and 1000 ppm sodium sulfite. Effluent from the first IMAG reactor was pH adjusted and used as the feedstock for the first IMGI reactor. Effluent from the latter reactor was pH adjusted and used as the feedstock for the second IMAG reactor. Lastly, effluent from the latter reactor was pH adjusted and used as a feedstock for the second stage IMGI reactor. Results are summarized below and compared with the product afforded by a single-bed IMAG reactor as well as the saccharification product using soluble AG at a concentration of 7000 IU/liter Maltrin-150(30 wt. % DSB).

TABLE 1

| Composition of Effluents in Staged Reactor Flow Scheme | |
|---|---|
| First IMAG effluent | |
| $DP_1$ (glucose) | 70–76% |
| <$DP_1$> | 74% |
| $DP_2$ | 3–6% |
| $DP_3$ | 0.5–1% |
| $DP_{4+}$ | 19–24% |
| First IMGI effluent | |
| fructose | 27–33% |
| <fructose> | 28.2% |
| glucose | 41–47% |
| Second IMAG effluent | |
| <$DP_1$> | 94.5% |
| isomaltose | 1.2% |
| Second IMGI effluent | |
| <fructose> | 42.2% |
| $DP_{2+}$ | 5.5% |

TABLE 2

| | Comparison of Various Process Flow Schemes | | |
|---|---|---|---|
| | Single bed IMAG (to maximum glucose) | Staged IMAG/IMGI (this invention) | Soluble AG |
| $DP_1$ | 93.6 | 94.5 | 95.1 |
| $DP_2$ | 4.1 | 2.9 | 3.5 |
| isomaltose | 1.9 | 1.2 | 1.6 |
| $DP_3$ | 0.5 | 0.3 | 0.5 |
| $DP_{4+}$ | 1.8 | 2.3 | 0.9 |

As Table 2 shows the staged IMAG/IMGI affords a product with isomaltose levels substantially below that from a single IMAG used to maximum glucose formation, and even gives less isomaltose than that from soluble AG.

What is claimed is:

1. A method of converting thinned starch to a solution containing up to about 6% disaccharides and higher oligosaccharides and at least 30% fructose, with the remainder being essentially glucose, comprising:
    (a) contacting a feedstock of thinned starch with an amyloglucosidase under saccharifying conditions for a time sufficient to produce from about 50% to about 85% glucose;

(b) contacting the hydrolyzed product from stage (a) with an immobilized glucose isomerase under isomerizing conditions until at least about 25% of the glucose initially present has been converted to fructose;

(c) contacting the partly isomerized product from stage (b) with an immobilized amyloglucosidase under saccharifying conditions until no more than about 6% disaccharides and higher oligosaccharides remain;

(d) contacting the product from stage (c) with an immobilized glucose isomerase under isomerizing conditions, and recovering the product produced thereby.

2. The method of claim 1 where the hydrolysis in stage (a) is continued for a time sufficient to produce from about 60% to about 80% glucose.

3. The method of claim 1 where the isomerization in stage (b) is continued for a time sufficient to convert from about 30% to about 45% of the glucose present to fructose.

4. The method of claim 1 where the isomerization of stage (d) is continued for a time sufficient to convert from about 30% to about 45% of the glucose present to fructose.

5. The method of claim 4 further characterized in that the product of stage (d) contains from about 40% to about 45% fructose.

6. The method of claim 5 where the product contains from about 42% to about 45% fructose.

7. The method of claim 1 where the amyloglucosidase is in solution.

8. The method of claim 1 where the amyloglucosidase is immobilized.

9. A method of making a mixture consisting essentially of not more than about 6% disaccharides and higher oligosaccharides, less than about 1.5% isomaltose, and at least about 12% fructose with the remainder being essentially glucose, comprising:

(a) contacting a feedstock of thinned starch with an amyloglucosidase under saccharifying conditions for a time sufficient to produce from about 50% to about 85% glucose;

(b) contacting the hydrolyzed product from stage (a) with an immobilized glucose isomerase under isomerizing conditions until at least about 25% of the glucose initially present has been converted to fructose;

(c) contacting the partly isomerized product from stage (b) with an immobilized amyloglucosidase under saccharifying conditions until no more than about 6% disaccharides and higher oligosaccharides remain, and recovering the resulting hydrolyzed product.

10. The method of claim 9 where the hydrolysis in stage (a) is continued for a time sufficient to produce from about 60% to about 80% glucose.

11. The method of claim 9 where the isomerization in stage (b) is continued for a time sufficient to convert from about 30% to about 45% of the glucose present to fructose.

12. The method of claim 9 where the amyloglucosidase is in solution.

13. The method of claim 9 where the amyloglucosidase is immobilized.

* * * * *